US007128897B2

(12) United States Patent
Osbakken et al.

(10) Patent No.: US 7,128,897 B2
(45) Date of Patent: *Oct. 31, 2006

(54) AEROSOLIZED ANTI-INFECTIVES, ANTI-INFLAMMATORIES, AND DECONGESTANTS FOR THE TREATMENT OF SINUSITIS

(75) Inventors: Robert S. Osbakken, Camarillo, CA (US); Mary Anne Hale, Woodland Hills, CA (US); Frederick T. Leivo, Carpinteria, CA (US); James D. Munk, Camarillo, CA (US)

(73) Assignee: Naryx Pharma, Inc., Carpinteria, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/231,804

(22) Filed: Aug. 28, 2002

(65) Prior Publication Data

US 2003/0031631 A1    Feb. 13, 2003

Related U.S. Application Data

(63) Continuation of application No. 09/577,623, filed on May 25, 2000, now Pat. No. 6,576,224.

(60) Provisional application No. 60/193,510, filed on Apr. 3, 2000, provisional application No. 60/193,508, filed on Apr. 3, 2000, provisional application No. 60/193,507, filed on Apr. 3, 2000, provisional application No. 60/193,509, filed on Apr. 3, 2000, provisional application No. 60/194,078, filed on Apr. 3, 2000, provisional application No. 60/142,881, filed on Jul. 6, 1999, provisional application No. 60/142,741, filed on Jul. 6, 1999, provisional application No. 60/142,624, filed on Jul. 6, 1999, provisional application No. 60/142,622, filed on Jul. 6, 1999, provisional application No. 60/142,621, filed on Jul. 6, 1999, provisional application No. 60/142,620, filed on Jul. 6, 1999, provisional application No. 60/142,618, filed on Jul. 6, 1999.

(51) Int. Cl.
*A61K 9/12* (2006.01)

(52) U.S. Cl. ........................ 424/45; 424/434; 424/450; 514/853

(58) Field of Classification Search .................. 424/45, 424/46, 434, 489, 450, 198.1; 514/853, 393, 514/300, 3, 51, 460; 128/200.14; 35/38
See application file for complete search history.

(56) References Cited

U.S. PATENT DOCUMENTS

| | | | |
|---|---|---|---|
| 4,312,860 A | 1/1982 | Clements | 424/199 |
| 4,424,216 A | 1/1984 | Cerami et al. | 424/211 |
| 4,438,100 A * | 3/1984 | Balslev et al. | 424/537 |
| 4,468,513 A | 8/1984 | Kirst et al. | 536/16.8 |
| 4,478,822 A | 10/1984 | Haslam et al. | 424/78 |
| 4,486,418 A | 12/1984 | Watanabe et al. | 424/180 |
| 4,493,831 A | 1/1985 | Takaya et al. | 424/180 |
| 4,554,269 A | 11/1985 | Takaya et al. | 514/35 |
| 4,571,334 A | 2/1986 | Yoshida et al. | 424/95 |
| 4,593,089 A | 6/1986 | Wang et al. | 536/13.6 |
| 4,617,293 A | 10/1986 | Wahlig et al. | 514/41 |
| 4,647,656 A | 3/1987 | Watanabe et al. | 536/16.1 |
| 4,656,160 A | 4/1987 | Takaya et al. | 514/41 |
| 4,684,643 A | 8/1987 | Buddenbaum et al. | 514/204 |
| 4,693,999 A | 9/1987 | Axelsson et al. | 514/174 |
| 4,767,612 A * | 8/1988 | Hagen et al. | 424/434 |
| 4,855,287 A | 8/1989 | Watanabe et al. | 514/41 |
| 4,906,476 A | 3/1990 | Radhakrishnan | 424/450 |
| 4,917,951 A | 4/1990 | Wallach | 428/402.2 |
| 4,944,949 A | 7/1990 | Story et al. | 424/451 |
| 4,950,477 A | 8/1990 | Schmitt et al. | 424/43 |
| 5,004,611 A | 4/1991 | Leigh | 424/450 |
| 5,006,343 A | 4/1991 | Benson et al. | 424/450 |
| 5,039,666 A | 8/1991 | Novick, Jr. | 517/37 |
| 5,049,388 A | 9/1991 | Knight et al. | 424/450 |
| 5,049,389 A | 9/1991 | Radhakrishnan | 424/450 |
| 5,110,806 A | 5/1992 | Clements | 514/78 |
| 5,112,804 A | 5/1992 | Kowarski | 514/3 |
| 5,141,674 A | 8/1992 | Leigh | 252/305 |
| 5,145,684 A | 9/1992 | Liversidge et al. | |
| 5,167,506 A | 12/1992 | Kilis et al. | 434/262 |
| 5,169,637 A | 12/1992 | Lenk et al. | 424/450 |
| 5,299,566 A | 4/1994 | Davis et al. | 128/200 |
| 5,397,771 A | 3/1995 | Bechgaard et al. | 514/2 |
| 5,428,006 A | 6/1995 | Bechgaard et al. | 514/3 |
| 5,508,269 A | 4/1996 | Smith et al. | 514/38 |
| 5,512,269 A | 4/1996 | Molina y Vedia et al. | 424/45 |
| 5,522,385 A | 6/1996 | Lloyd et al. | 128/203.26 |
| 5,525,329 A | 6/1996 | Snyder et al. | 424/45 |
| 5,567,716 A | 10/1996 | Della Valle et al. | 514/332 |
| 5,595,977 A | 1/1997 | Dyrsting et al. | 514/39 |
| 5,614,216 A | 3/1997 | Janoff | 424/450 |
| 5,624,962 A | 4/1997 | Dyrsting et al. | 514/39 |
| 5,655,523 A | 8/1997 | Hodson et al. | 128/315 |

(Continued)

FOREIGN PATENT DOCUMENTS

EP    0 267 050 A1    5/1988

(Continued)

OTHER PUBLICATIONS

Drug Information Handbook, by Lexi-comp, 1993, pp. 23-24 and 676.*

(Continued)

*Primary Examiner*—Sreeni Padmanabhan
*Assistant Examiner*—Mina Haghighatian
(74) *Attorney, Agent, or Firm*—Wilson, Sonsini, Goodrich & Rosati

(57) ABSTRACT

Pharmaceutical compositions are described that contain one agent for treatment of sinusitis and a surfactant. The compositions are prepared to have a surface tension that renders the composition effective for treatment of sinusitis.

47 Claims, 1 Drawing Sheet

U.S. PATENT DOCUMENTS

| | | | |
|---|---|---|---|
| 5,685,291 A | 11/1997 | Marsh | 128/200.15 |
| 5,693,608 A | 12/1997 | Bechgaard et al. | 514/2 |
| 5,789,391 A | 8/1998 | Jacobus et al. | 514/51 |
| 5,843,881 A | 12/1998 | Dubois et al. | 512/1 |
| 5,861,275 A | 1/1999 | Hansen | 435/69.1 |
| 5,883,084 A | 3/1999 | Peterson et al. | 514/78 |
| 5,900,406 A | 5/1999 | von Ahsen et al. | 514/35 |
| 5,900,407 A | 5/1999 | Yerxa et al. | 514/47 |
| 5,906,198 A | 5/1999 | Flickinger | 128/200.21 |
| 5,925,334 A | 7/1999 | Rubin et al. | 424/45 |
| 5,958,897 A | 9/1999 | Jacobus et al. | 514/49 |
| 5,972,904 A | 10/1999 | Jacobus et al. | 514/51 |
| 5,976,573 A | 11/1999 | Kim | 424/489 |
| 5,981,506 A | 11/1999 | Jacobus et al. | 514/47 |
| 5,985,259 A | 11/1999 | Cagle et al. | 424/78.04 |
| 6,083,922 A | 7/2000 | Montgomery | 514/38 |
| 6,126,930 A | 10/2000 | Dubois et al. | 424/73 |
| 6,143,329 A | 11/2000 | Kim | 424/489 |
| 6,207,703 B1 | 3/2001 | Ponikau | 514/460 |
| 6,241,969 B1 | 6/2001 | Saidi et al. | 424/45 |
| 6,274,634 B1 | 8/2001 | Yasueda et al. | 514/781 |
| 6,277,855 B1 | 8/2001 | Yerxa | 514/256 |
| 6,291,500 B1* | 9/2001 | Ponikau | 514/393 |
| 6,331,529 B1 | 12/2001 | Yerxa et al. | 514/47 |
| 6,375,984 B1 | 4/2002 | Kan | 424/489 |
| 6,387,886 B1 | 5/2002 | Montgomery et al. | 514/34 |
| 6,395,300 B1 | 5/2002 | Straub et al. | 424/489 |
| 6,395,746 B1 | 5/2002 | Cagle et al. | 514/300 |
| 6,420,347 B1 | 7/2002 | Jacobus et al. | 514/51 |
| 6,423,694 B1 | 7/2002 | Drutz et al. | 514/51 |
| 6,436,910 B1 | 8/2002 | Yerxa et al. | 514/47 |
| 6,448,276 B1 | 9/2002 | Yerxa | 514/357 |
| 6,462,183 B1 | 10/2002 | Toth et al. | 536/17.2 |
| 6,555,566 B1 | 4/2003 | Ponikau | 514/393 |
| 2001/0002400 A1 | 5/2001 | Ponikau | 514/393 |
| 2001/0006944 A1 | 7/2001 | Ponikau | 514/31 |
| 2001/0031779 A1 | 10/2001 | Ponikau | 514/393 |
| 2002/0052338 A1 | 5/2002 | Yerxa et al. | 514/47 |
| 2002/0052390 A1 | 5/2002 | Ponikau | 514/310 |
| 2002/0061281 A1 | 5/2002 | Osbakken et al. | |
| 2002/0065244 A1 | 5/2002 | Yerxa et al. | 514/47 |
| 2002/0102294 A1* | 8/2002 | Bosch et al. | 424/450 |
| 2002/0103157 A1 | 8/2002 | Yerxa et al. | 514/47 |

FOREIGN PATENT DOCUMENTS

| | | |
|---|---|---|
| EP | 0 267 050 B1 | 9/1994 |
| EP | 0626173 A1 | 11/1994 |
| EP | 0507707 | 7/1995 |
| EP | 0470154 | 6/1996 |
| EP | 0563131 | 9/1996 |
| EP | 0682514 | 9/2001 |
| EP | 0925308 | 6/2002 |
| EP | 0705614 | 9/2002 |
| JP | 10130148 | 5/1998 |
| WO | 9729756 | 8/1997 |
| WO | 9735591 | 10/1997 |
| WO | 9834593 | 8/1998 |
| WO | 0000181 | 1/2000 |
| WO | 0050024 | 8/2000 |
| WO | 01/02024 | 1/2001 |
| WO | 0119344 | 3/2001 |
| WO | 0180844 | 11/2001 |
| WO | 02068031 | 9/2002 |
| WO | WO 03/020219 | 3/2003 |

OTHER PUBLICATIONS

Alexandrakis et al., "Nasolacrimal Duct Obstruction and Orbital Cellulitis Associated With Chronic Intranasal Cocaine Abuse," *Arch. Ophthalmol. 117*: 1617-1622 (1999).

Baraniuk et al., "Addition of intranasal glucocortcoids to standard antibiotic therapy for sinusitis", *Current Allergy and Asthma Rep 1(3)*: 191-2 (May, 2001).

Boyce et al., "MRSA patients: proven methods to treat colonization and infecion," *Journal of Hospital Infection 48(Supplement A)*: S9-S14 (2001).

Certified English Translation for Japanese Patent Application (Kokai) No. 10-130148 entitled: "Composition for Nebulizers".

Cimochowski et al., "Intranasal Mupirocin Reduces Sternal Wound Infection After open Heart Surgery in Diabetics and Nondiabetics," *Ann. Thorac. Surg. 71*: 1572-9 (2001).

Derwent# 009206491, W.P.I. Acc No.: 1992-333912/199241, for European Patent Application, EP 507707 A, "Control unit for therapeutic nebuliser—has sonic vibration control chamber made separate from over-pressure control chamber and linked to pulsed air source".

Derwent# 013773627, W.P.I. Acc No.: 2001-257838/200126, for PCT Patent Application, WO 200119344 A1, "Preparing powders for nasal atomization, useful e.g. for administering Vitamin B12, using water insoluble, absorbent excipient to carry active ingredient".

Desrosiers et al., "Treatment of chronic rhinosinusutus refractory to other treatments with topical antibiotic therapy delivered by means of a large-particle nebulizer: Results of a controlled trial," *Otolaryngol Head Neck Surg 125*: 265-9 (2001).

Desrosiers et al., "Treatment of Failures of Endoscopic Sinus Surgery (ESS) with Topical Antibiotics Delivered by Large-Diameter Particle Aerosol Therapy," ENT Academy Meeting (May 1999).

Dolor et al., "Comparison of Cefuroxime With or Without Intranasal Fluticasone for the Treatment of Rhinosinusitis," *Journal of the American Medical Association 286*: 3097-3105 (2001).

Dunbar, C.A. and A.J. Hickey, "Evaluation of Probability Density Functions To Approximate Particle Size Distributions of Representative Pharmaceutical Aerosols," *J. Aerosol. Sci 31(7)*: 813-831 (2000).

Farr, B.M., "Mupirocin to Prevent S. *Aureus* Infections," *New England Journal of Medicine 346(24)*: 1905-1906 (2002).

Guevara et al., "Ambulatory Aerosol Therapy in the Treatment of Chronic Pathology in O.R.L. Sphere," *Annales O.R.L. Iber.Amer. XVIII*, 3:231-238 (1991).

Hiramatsu et al., "MRSA Infections in an Intensive Care Unit," *Masui 49*: 867-71 (2000).

Hitomi et al. "Control of a methicillin-resistant *Staphylococcus aureus* outbreak in a neonatal intensive care unit by unselective use of nasal mupirocin ointment," *Journal of Hospital Infection 46*: 123-129 (2000).

Holmström, M., "Nasal polyposis—of interest to several specialities. Improvements in diagnosis and new treatment methods," *Lakartidningen 97(34)*: 3611-5 (2000).

Jeong et al., "Intranasal mupirocin for prevention of hospital MRSA infection," *ASHP-Midyear Clinical Meeting, Abstract of Meeting Presentation 33(Dec)*: INTL-21 (1998).

Kaiser et al., "Impact of Zanamivir on Antibiotic Use for Respiratory Events Following Acute Influenza in Adolescents and Adults," *Arch. Intern. Med. 160*: 3234-3240 (2000).

Knowles, S., "Five-day otitis media therapy. Cisapride monitoring in children. Efficacy of sumatriptan nasal spray. Testosterone for AIDS wasting.," *Pharmacy Practice* (Canada) 14: 28-30 (Nov. 1998).

Kondo et al., "Transitional Concentration of Antibacterial Agent to the Maxillary Sinus via a Nebulizer," *Acta Otolaryngol. Suppl*, 525: 64-67 (1996).

Lim et al., "In vivo evaluation of novel hyaluronan/chitosan microparticulate delivery systems for the nasal delivery of gentamicin in rabbits," *International Journal of Pharmaceutics 231*: 73-82 (2002).

Maccabee, M. and P.H. Hwang, "Medical Therapy of Acute and Chronic Frontal Rhinosinusitis," *Otolaryngologic Clinics of North America 34*: 41-7 (2001).

Mahajan et al., "Intranasal Administration of Fusidic Acid Cream in Leprosy," *Indian Journal of Leprosy 72(4)*: 451-455 (2000).

Meltzer et al., "Added relief in the treatment of acute recurrent sinusitis with adjunctive mometasone furoate nasal spray," *J. Allergy Clin. Immunol.* 106: 630-7 (2000).

Nagl et al., "Acitivity of N-chlorotaurine against herpes simplex- and adenoviruse", *Antiviral Research*, 38:25-30 (1988).

Nagl et al., "Bactericidal Activity of Micromolar N-Chlorotaurine: Evidence for Its Antimicrobial Function in the Human Defense System", *Antimicrobial Agents and Chemotherapy*, 44(9):2507-2513 (2000).

Nardi et al., "Reduction in Gram-positive pneumonia and antibiotic consumption following the use of a SDD protocol including nasal and oral mupirocin," *European Journal of Emergency Medicine* 8: 203-14 (2001).

Negley et al., "RinoFlow™ Nasal Wash and Sinus System as a mechanism to deliver medications to the paranasal sinuses: Results of a radiolabeled pilot study," *ENT Journal*, 78(8): 550-554 (1999).

Neher et al., "N-Chlorotaurine, a Novel Endogenoius Antimicrobial Agent", 127:530-533 (2001).

Nichol et al., "Effectiveness of Live, Attenuated Intranasal Influenza Virus Vaccine in Healthy, Working Adults," *Journal of the American Medical Association* 282(2): 137-144 (1999).

O'Riordan et al., "Effect of Nebulizer Configuration on Delivery of Aerosolized Tobramycin," *Journal of Aerosol Medicine*, 10(1): 13-23 (1997).

Oszi et al., "Quantitative determination of polysorbate 20 in nasal pharmaceutical preparations by high-performance liquid chromatography", 18:715-720 (1998).

Package Insert for: *Proventil®* (*brand of albuterol sulfate*), Schering Corporation, 1986.

Package Insert for: *Pulmicort Respules™* (*Budesonide inhalation suspension*), AstraZeneca, 2000.

Package Insert for: *Pulmicort Turbuhaler 200 mcg* (*Budesonide inhalation powder*), AstraZeneca, 2001.

Perkins et al., "Hemothorax in 2 Horses," *J. Vet. Intern. Med.* 13: 375-378 (1999).

Perl et al., "Intranasal Mupirocin to Prevent Postoperative *Staphylococcus aureus* Infections," *New England Journal of Medicine* 346(24): 1871-7 (2002).

Press Release, "Atlantic Technology Ventures, Inc. Licenses World Wide Rights to ATV-02 Antimicrobial Agent", *Atlantic Technology Ventures*, pp. 1-3, http://biz.yahoo.com/bw/020709/92194_1.html (2002).

Raikhlin-Eisenkraft, B. and Y. Bentur, "*Ecbalium elaterium* (Squirting Cucumber)- Remedy or Poison," *Clinical Toxicology* 38(3): 305-8 (2000).

Tracy et al., Intranasal beclomethasone as an adjunct to treatment of chronic middle ear effusion, *Annals of Allergy, Asthma, & Immunology* 80: 198-206 (1998).

Tradename: ATV-02, "BioSpace Clinical Development: ATV-02 Detail", *Atlantic Technology Ventures*, http://www.biospace.com/ccis/detail.cfm?Clinical1ID=794920 (2002).

Tsurita et al., "Early Augmentation of Interleukin (IL)-12 Level in the Airway of Mice Administered Orally with Clarithromycin or Intranasally with IL-12 Results in Alleviation of Influenza Infection," *The Journal of Pharmacology and Experimental Therapeutics* 298(1): 362-368 (2001).

Wang, J. and G. Bu, Influence of intranasal medication on the structure of the nasal mucosa, *Chinese Medical Journal* 115(4): 617-619 (2002).

Wang, J. and G. Bu, "Influence of the nasal mucociliary system on intranasal drug administration, " *Chinese Medical Journal* 113(7): 647-649 (2000).

Yilmaz et al., "Intranasal budesonide spray as an adjunct to oral antibiotic therapy for acute sinusitis in children," *Eur. Arch. Otorhinolaryngol.* 257: 256-259 (2000).

Yokota et al., "Antibacterial Activities of Cefmenoxime against Recent Fresh Clinical Isolates from Patients of Sinusitis," *The Japanese Journal of Antibiotics*, 48-5: 602-609 (1995).

Kohler, D. "Systemic therapy with aerosols", *Aerosols of Medicine. Principles, Diagnosis and Therapy*. Editors Moren et al., Elsevier Publishers, pp. 303-319, (1993).

Rakel, R.E., "Sinusitis", *Saunders Manual of Medical Practice*, W.B. Saunders Co., pp. 90-92, (1996).

Dixson, R., "The why, what and how of endoscopic sinus surgery," Seminars in Perioperative Nursing 9(4):163-167 (2000).

Kaliner, M., "Treatment of sinusitis in the next millennium," Allergy and Asthma Proc. 19(4):181-184 (1998).

Leopold et al. "Outcomes assessment." Otolaryngol Head Neck Surg. 117: S58-S68 (1997).

Scheinberg et al., "Nebulized antibiotics for the treatment of acute exacerbations of chronic rhinosinusitis," ENT Journal 81(9):648-52 (2002).

Suman et al., "Comparison of Nasal Deposition and Clearance of Aerosol Generated by a Nebulizer and an Aqueous Spray Pump," Pharmaceutical Research 16(10):1648-1652 (1999).

Vaughan et al., "Use of nebulized antibiotics for acute infections in chronic sinusitis," Otolaryngology-Head and Neck Surgery 127(6):558-568 (2002).

Youngs, R., "Sinusitis in adults," Curr. Opin. Pulm. Med. 6(3):217-220 (2000).

Press Release "Scripps Memorial Hospital's Chief of Otolaryngology Develops Usage Algorithm for Intranasal Nebulized Medications for Chronic Sinusitis" (Feb. 12, 2003) http://www.sinuspharmacy.com/presswahl.html [accessed on Sep. 8, 2004].

Press Release "SinusPharmacy Adds Nasal Irrigation Option to SinuNEB System" (Sep. 18, 2002) http://www.sinuspharmacy.com/pressirrigator.html [accessed on Sep. 8, 2004].

Press Release "Study Finds Nebulized Antibiotics Effective Against Chronic Sinusitis" (Sep. 17, 2002) http://www.sinuspharmacy.com/pressnebulizedsinusitis.html [accessed on Sep. 8, 2004].

Press Release "SinusPharmacy Announces Breakthrough in Treating Chronic Sinusitis" (Sep. 25, 2000) http://www.sinuspharmacy.com/press001.html [accessed on Sep. 8, 2004].

Bommer, R., "Latest Advances in Nasal Drug-Delivery Technology," Medical Device Technology 10(4):22-28 (1999).

Kublik et al., "Nasal delivery systems and their effect on deposition and absorption," Advanced Drug Delivery Reviews 29:157-177 (1998).

Suman et al., "Comparison of Nasal Deposition and Clearance of Aerosol Generated by a Nebulizer and an Aqueous Spray Pump," Pharmaceutical Research 16(10):1648-1652 (1999).

Allen et al, "Effect of Surfactant on Tetracycline Absorption across Everted Rat Intestines, " Journal of Pharmaceutical Sciences 70(3): 269-271 (1981).

Amidon et al., "Theoretical and Experimental Studies of Transport of Micelle-Solubilized Solutes,"Journal of Pharmaceutical Science 71(1): 77-84 (1982).

Attwood et al., "Solubilization of Indomethacin by Polysorbate 80 in Mixed Water-Sorbitol Solvents," J. Pharm. Pharmacol. 41: 83-86 (1989).

Florence et al., "Non-ionic surfactants and memebrane transport of thioridazine in goldfish," J. Pharm. Pharmac. 27: 152-159 (1975).

Kimura et al., "Effect of synthetic surfactants on drug absorption in the presence of a physicologic surfactant, sodium taurocholate, in rats," J. Pharmacobio-Dyn. 8: 661-668 (1985).

Pontiroli et al., "Human insulin plus sodium glycocholate in a nasal spray formulation: improved bioavailability and effectiveness in normal subjects," Diabete & Metabolisme (Paris) 13: 441-443 (1987).

Salzman et al., "Intranasal Aerosolized Insulin," The New England Journal of Medicine 312: 1078-1084 (1985).

Smith et al., "Safety of Aerosol Tobramycin Administration for 3 Months of Patients With Cystic Fibrosis,"Pediatric Pulmonology 7: 265-271 (1989).

* cited by examiner

AEROSOLIZED ANTI-INFECTIVES, ANTI-INFLAMMATORIES, AND DECONGESTANTS FOR THE TREATMENT OF SINUSITIS

RELATED APPLICATIONS

This application is a continuation of allowed U.S. application Ser. No. 09/577,623, now U.S. Pat. No. 6,576,224 to Osbakken et al., entitled "AEROSOLIZED ANTI-INFECTIVES, ANTI-INFLAMMATORIES, AND DECONGESTANTS FOR THE TREATMENT OF SINUSITIS." This application claims priority under 35 U.S.C. §119(e) to each of U.S. provisional application Ser. Nos. 60/142,618, 60/142,620, 60/142,621, 60/142,622, 60/142,624, 60/142,741, and 60/142,881, each filed on Jul. 6, 1999, and to each of U.S. provisional application Ser. Nos. 60/194,078, 60/193,509, 60/193,508, 60/193,507 and 60/193,510, each filed Apr. 3, 2000. The disclosure of each of the above-referenced utility and provisional applications is incorporated herein by reference in its entirety.

FIELD

The present invention relates to pharmaceutical compositions comprising one or more active ingredients selected from the group consisting of anti-infective, anti-inflammatory and mucolytic agents, and particularly to compositions formulated as a solution in a unit dose or multi-dose vials for aerosol administration to treat chronic sinusitis.

BACKGROUND

There are a number of air-filled cavities called sinuses in the skull (*Stedman's Medical Dictionary, 27th Edition*, page 1644, (1999), Lippincott Williams & Wilkins, Baltimore, Md.). Four pairs of sinuses known as the paranasal sinuses, connect the space (known as the nasal passage) running from the nostrils and up through the nose. These four pairs of paranasal sinuses are the frontal sinuses, the maxillary sinuses, the ethmoid sinuses, and the sphenoid sinuses. They are located, respectively, in the forehead, behind the cheekbones, between the eyes, and behind the eyes. A membrane lining the sinuses secretes mucus, which drains into the nasal passage from a small channel in each sinus. Healthy sinuses are sterile and contain no bacteria. In contrast, the nasal passage, normally contains many bacteria that enter through the nostrils as a person breathes.

A number of factors and/or processes are involved in maintaining healthy sinuses. The mucus secreted by the membrane lining must be fluid but sticky, in order to flow freely yet absorb pollutants and entrap bacteria. It must also contain sufficient amounts of bacteria-fighting substances, such as antibodies. Additionally, small hair-like projections called cilia, located in the nostril, must beat in unison to propel mucus outward, in order to expel bacteria and other particles. Moreover, the mucous membranes themselves must be intact, and the sinus passages must be open to allow drainage and the circulation of air through the nasal passage. When one or more of these processes or factors are amiss, causing obstruction of the sinus passage, an infection called sinusitis develops.

Sinusitis is an inflammation of the membrane lining one or more paranasal sinuses. There are three different types of sinusitis: acute, recurrent acute, and chronic. Acute sinusitis is characterized as lasting less than three weeks or occurring less than four times a year. Acute sinusitis can be successfully treated using antibiotics, leaving no damage to the linings of the sinus tissue. Recurrent acute sinusitis occurs more often but leaves no significant damage. Chronic sinusitis lasts longer than three weeks and often continues for months. In cases of chronic sinusitis, there is usually tissue damage. According to the Center for Disease Control (CDC), thirty seven million cases of chronic sinusitis are reported annually.

Causes of Sinusitis

The most common cause for sinusitis is a viral cold or flu that infects the upper respiratory tract and causes obstruction. Obstruction creates an environment that is hospitable for bacteria, the primary cause of acute sinusitis (Etkins et al., 1999 *Nidus Information Services, Inc. Well-Connected Report: Sinusitis*. June 1999. (Online) www.well-connected.com.). The bacteria most commonly found in acute sinusitis are *Streptococcus pneumoniae* (also called pneumococcal pneumonia or pneumococci), *H. influenzae* (a common bacteria associated with many respiratory infections in young children), and *Moraxella* (or *Branhamella*) *catarrhalis*. Less common bacterial culprits include other streptococcal strains including *Staphylococcus aureus*.

Fungi are an uncommon cause of sinusitis, but its incidence is increasing. The fungus *Aspergillus* is the common cause of fungal sinusitis. Others include *Curvularia, Bipolaris, Exserohilum*, and *Mucormycosis*. Fungal infections can be very serious and should be suspected in people with sinusitis who also have diabetes, leukemia, AIDS, or other conditions that impair the immune systems. Fungal infections can also occur in patients with healthy immune systems. There have been a few reports of fungal sinusitis caused by *Metarrhizium anisopliae* which is used in biological insect control.

Chronic or recurrent acute sinusitis can be a lifelong condition and may result from untreated acute sinusitis that causes damage to the mucous membranes, medical disorders that cause chronic thickened stagnant mucus, or abnormalities in the nasal passage such as polyps, enlarged adenoids, cleft palate, or tumors. The same organisms that cause acute sinusitis are often present in chronic sinusitis. In addition, about 20% of chronic sinusitis cases (Etkins et al., 1999, Id.) are caused by *Staphylococcus aureus* (commonly called Staph infection). Along with these bacteria, certain anaerobic bacteria, particularly the species *Peptostreptococcus, Fusobacterium*, and *Prevotella*, are found in 88% of cultures in chronic sinusitis cases (Etkins et al., 1999, Id.). Fungi can also cause chronic and recurrent sinusitis. An uncommon form of chronic and highly recurrent sinusitis is caused by an allergic reaction to fungi, usually, *aspergillus*, growing in the sinus cavities. Fungal sinusitis usually occurs in younger people with healthy immune systems and is more likely to be found in warm climates.

Symptoms of Sinusitis

In acute sinusitis, symptoms almost always present are nasal congestion and discharge which is typically thick and contains pus that is yellowish to yellow-green. Severe headache occurs, and there is pain in the face. A persistent cough occurs particularly during the day. Other upper respiratory symptoms and fever may be present. Sneezing, sore throat, muscle aches, and fatigue are rarely caused by sinusitis itself, but may result from symptoms or causes, such as muscle aches caused by fever, sore throat caused by postnasal drip, and sneezing resulting from allergies.

The symptoms of recurrent acute and chronic sinusitis tend to be vague and generalized, last longer than eight weeks, and occur throughout the year, even during nonallergy seasons. Nasal congestion and obstruction are common. Yellowish discharge, chronic cough, bad breath, and postnasal drip may occur. Sufferers do not usually experience facial pain unless the infection is in the frontal sinuses, which results in a dull, constant ache. However, facial tenderness or pressure may be present.

Site-specific symptoms depend on the location of the infection. Frontal sinusitis causes pain across the lower forehead. Maxillary sinusitis causes pain over the cheeks and may travel to the teeth, and the hard palate in the mouth sometimes becomes swollen. Ethmoid sinusitis causes pain behind the eyes and sometimes redness and tenderness in the area across the top of the nose. Sphenoid sinusitis rarely occurs by itself. When it does, the pain may be experienced behind the eyes, across the forehead, or in the face. Rare complications of sinusitis can produce additional symptoms which may be severe or even life threatening.

Treatments of Sinusitis

The primary objectives for treatment of sinusitis are reduction of swelling, eradication of infection, draining of the sinuses, and ensuring that the sinuses remain open. Less than half of patients reporting symptoms of sinusitis need aggressive treatment and can be cured using home remedies and decongestants alone. Steam inhalation and warm compresses applied over the sinus are often sufficient to relieve discomfort. Many over-the-counter decongestants are available, either in tablet form or as sprays, drops, or vapors, which bring the medication into direct contact with nasal tissue.

Antibiotics are prescribed if decongestants fail to relieve symptoms or if other problems exist, including signs of infection (such as yellowish nasal discharge). They prevent complications, relieve symptoms, and reduce the risk of chronic sinusitis. Most patients with sinusitis caused by bacteria can be successfully treated with antibiotics used along with a nasal or oral decongestant.

Chronic sinusitis is often difficult to treat successfully, however, as some symptoms persist even after prolonged courses of antibiotics. The usefulness of antibiotics in treating chronic sinusitis is debated. Steroid nasal sprays are commonly used to treat inflammation in chronic sinusitis. For patients with severe chronic sinusitis, a doctor may prescribe steroids, such as prednisone. Since oral steroids can have serious side effects, they are prescribed only when other medications have not been effective.

When medical treatment fails, surgery may be the only alternative in treating chronic sinusitis. Studies suggest that the most patients who undergo surgery have fewer symptoms and better life. Presently, the most common surgery done is functional endoscopic sinus surgery, in which the diseased and thickened tissues from the sinuses are removed to allow drainage. This type of surgery is less invasive than conventional sinus surgery, and serious complications are rare.

Considerations and Concerns of Treatments

Sprays, drops, and vapors work quickly but often require frequent administration. Nasal decongestants may dry out the affected areas and damage tissues. With prolonged use, nasal decongestants become ineffective. The tendency is to then increase the frequency of use to as often as once an hour. Withdrawal from the drugs after three to five days of over-frequent use can itself cause symptoms of sinusitis and the return of nasal congestion phenomenon known as rebound effect. Short-acting nasal decongestants may cause rebound effect after only eight hours. Rebound effect leads to dependency when the patient takes the decongestant to treat the rebound effect, the drug becomes ineffective, the patient withdraws, and the condition rebounds again, with the nasal passages becoming swollen and burning. Eventually, the condition can become worse than before the medication was taken. Nasal decongestants are generally recommended for no more than one to three days of use because of this risk.

Some oral decongestants may cause constriction of other vessels in the body, temporarily raising blood pressure in people with hypertension. Other side effects of oral decongestants include insomnia, agitation, abnormal heart rhythms (particularly in people with existing cardiac problems), and urinary retention in men with enlarged prostates. Decongestant sprays and drops, too, are absorbed into the body and can sometimes cause these side effects.

The most common side effect for nearly all antibiotics is gastrointestinal distress. Antibiotics also double the risk for vaginal infections in women. Certain drugs, including some over-the-counter medications, interact with antibiotics, and all antibiotics carry the risk for allergic reactions, which can be serious in some cases. Thus, patients should inform their physician of all medications they are taking and of any drug allergies.

Oral antibiotics are usually prescribed for 7 to 10 days. Patients must take all of the tablets prescribed; failure to do so may increase the risk for reinfection and also for development of antibiotic-resistant bacteria. It should be noted, however, that even after antibiotic treatments, between 10% and 25% of patients still complain of symptoms.

Of major concern to physicians and the public is the emergence of bacterial strains that have become resistant to common antibiotics due to frequent exposure. It should be noted that the average person is not yet endangered by this problem. The risk is greatest in hospitals and nursing homes, but it is still not high. Nonetheless, the prevalence of such antibiotic-resistant bacteria has increased dramatically worldwide, and caution should be exercised.

Nebulization Therapy

Nebulization is a conventional treatment for pulmonary infections related to cystic fibrosis, because it is relatively easy and safe to use, and because it delivers antibiotics topically to the site of infection, with little systemic absorption of the antibiotics. Nebulization has also been known to have been used for sinus infections and pulmonary infections, related to bronchiectasis. Thus, there are few systemic side effects.

Small Aerosolized Particles for Treating Sinusitis

Yokota et al., *Japanese Journal of Antibiotics* 609(15):48 (1995) reports administration of cefmenoxime using a nebulizer to treat sinusitis patients. These authors evaluated cefmenoxime against clinical isolates from sinusitis patients, and found that minimum inhibitory concentrations were lower when a one percent (1%) solution was used with a nebulizer. The paper speculates that sufficient concentrations exceeding such minimum inhibitory concentrations would be obtained by nebulizer treatment using a cefmenoxime nasal solution.

Guevara et al., *Anales O.R.L. Iber.-Amer.* XVIII, 3:231–238 (1991), describes aerosol therapy for treating patients suffering from chronic sinusitis. The disclosed aerosol therapy involves delivery of a therapeutic composition comprising 500 mg of Cefotaxime, 5 mg methylprednisolone, and 1.5 ml N-acetylcysteina using an air-jet nebulizer for 15–20 minutes, every 8 hours, over a total period of 15 days. The air-jet nebulizer produces aerodynamic particle diameters of average mass of four microns. Guevara et al. reports a success rate of 96%. However, Guevara et al. does not disclose adding a surfactant to assist deposition, penetration, and retention of the antibiotic in the sinuses. It is also noted that the aerosol therapy of Guevara et al. requires frequent treatments over a long period of time.

Kondo et al., *Acta Otolaryngol. Suppl.* 525:64–67 (1996), reports treatment of paranasal sinusitis using fosfomycin (FOM) aerosol. Kondo et al. describes delivery of 4 ml of 3% FOM solution using either a jet-type nebulizer or a ultrasonic nebulizer. The jet-type nebulizer produces aerosol particles having about 0.5 to 0.7 μm in diameter, while the ultrasonic-type nebulizer produces particles having about 2–4 μm in diameter. The results of Kondo et al. indicate that the ultrasonic-type nebulizer delivers a higher concentration of FOM to the maxillary sinus surface and is therefore more effective in treating paranasal sinusitis than the jet-type nebulizer. Although Kondo et al. suggests that the preferred aerosol particle size is about 2–4 μm in diameter for deposition of a higher level of antibiotic in the maxillary sinus, Kondo et al. does not disclose an administration schedule or the addition of a surfactant to the FOM solution to further increase the deposition of FOM in the sinuses.

Small Aerosolized Particles for Pulmonary Treatment

Smith et al., U.S. Pat. No. 5,508,269, discloses the use of aminoglycoside aerosol formulations to treat patients suffering from endobronchial infection. Smith et al. describes delivery of the aminoglycoside formulation using a jet or ultrasonic nebulizer that produces aerosol particle size between 1 and 5 μm. The formulation comprises 200 to 400 mg of aminoglycoside dissolved in about 5 ml of solution containing 0.225% sodium chloride and it has a pH between 5.5 to 6.5. Although Smith teaches delivery of aminoglycoside to the endobronchial space using a nebulizer for the treatment endobronchial infection, Smith does not teach an aerosol formulation for treatment of sinusitis and does not disclose a treatment schedule. It is also noted that the aerosol particle size disclosed in Smith et al. is a broad range. It is not predictable what fraction of the aerosol particles between 1 to 5 μm will deposit in the sinuses, and what fraction of the aerosol particles will have a diameter of 1 μm, 2 μm, etc.

Rubin et al., U.S. Pat. No. 5,925,334, describes the use of aerosolized surfactant to promote pulmonary airway clearance. The method of Rubin et al. comprises administering a formulation containing a surfactant using a PARI LC Jet nebulizer for 15 minutes, 3 times a day for 14 consecutive days, to patients suffering from bronchitis or cystic fibrosis. However, Rubin does not teach the use of aerosolized antibiotic or aerosolized antibiotic and surfactant combination to treat sinusitis.

Schmitt et al., U.S. Pat. No. 4,950,477, teaches a method of preventing and treating pulmonary infection by fungi using aerosolized polyenes. The method comprises administering to a patient suffering from pulmonary infection by Asperigillus about 0.01 mg/kg to 6.0 mg/kg of a polyene in an aerosol of particles having an aerodynamic diameter between about 0.5 μm to about 8 μm. Schmitt et al. specifically discloses the administration of amphotericin B. Although Schmitt et al. teaches aerosolized polyenes for treatment of pulmonary infection, Schmitt et al. does not provide guidance for using aerosolized polyenes for treating sinusitis.

O'Riordan et al., *Journal of Aerosol Medicine,* 20(I): 13–23 (1997), reports the effect of nebulizer configuration on delivery of aerosolized tobramycin to the lung. O'Riordan et al. discloses the delivery of tobramycin using either an ultrasonic nebulizer delivering aerosol particles having between 1.45 to 4.3 μm or a jet nebulizer delivering aerosol particles having between 1.25 μm. The results of O'Riordan et al. show that nebulizer configuration affects both the amount of aerosolized tobramycin inhaled as well as the particle size. Specifically, nebulizers that produce large particles are prone to considerable deposition on tubing and connections. O'Riordan et al. recommends that nebulizer configuration be specified in treatment protocols.

Large Particle Aerosolization

In contrast to the references discussed above, Negley et al., *ENT Journal,* 78(8):550–554 (1999), and Desrosiers et al., (presented at the ENT Academy Meeting, May 1999) teach large particle nebulization therapy for treatment of sinusitis. Negley observes that deposition of medication into the sinuses is best achieved when the aerosolized particles are 16 to 25 μm in size. Desrosiers et al. reports that large particle saline aerosol therapy alone is effective in treating refractory sinusitis and that the addition of tobramycin to the saline solution had minimal benefit.

The journal articles and patents discussed above teach various aerosol therapies for the treatment of sinusitis. However, there does not appear to be agreement among the various authors as to the optimal size or size distribution of the aerosolized particles or even whether antibiotics are effective in treating sinusitis. What has been needed is a clinically effective anti-infective treatment protocol for sinusitis, a more optimal therapy schedule, and an appropriate nebulizer configuration for the deposition of aerosolized anti-infective particles into the sinuses for the successful and consistent treatment of chronic sinusitis.

SUMMARY

Provided are pharmaceutical compositions that include one or more active ingredients such as anti-infective, anti-inflammatory and mucolytic agents. Such compositions preferably are formulated as a solution in a unit dose or multi-dose vial for aerosol administration to the nasal sinuses. It is contemplated that such formulations are packaged with labels or inserts or other forms of directions for their use in the treatment of sinusitis.

In a preferred embodiment, the surface tension of the solution is between about 10 to 70 dynes/cm, in order to yield an aerosol having a preferred Mass Median Aerodynamic Diameter within the range of about 1.0 to 4.0 microns. The use of such an aerosolized spray has minimal systemic side effects. Surface tension of a given formulation may be adjusted by adding a surfactant in addition to the active ingredients in order to bring it into the preferred range.

Generally, it is contemplated that formulations according to the present invention will preferably have a pH in the range of about 3.0 to 8.5; an osmolality of the solution between about 150 mOsm/kg to 880 mOsm/kg; and a NaCl equivalency to the solution is preferably between about 0.9% NaCl to 3.0% NaCl.

Preferred anti-infective agents include Penicillins, Cephalosporins, Macrolides, Sulfonamides, Quinolones, Aminoglycosides, BetaLactam antibiotics, Linezolid, Vancomycin, Amphotericin B, and Azole antifungals. Preferred anti-inflammatory agents include Glucocorticoids, Disodium Cromoglycate and Nedcromil Sodium. Preferred mucolytic agents are Acetylcysteine and Dornase Alpha. Preferred decongestant agents are Phenylephrine, Naphazoline, Oxymetazoline, Tetrahydrozoline and Xylometoazoline.

Exemplary pharmaceutical compositions contain one or more active ingredients selected from the group consisting of anti-infective, anti-inflammatory and mucolytic agents, wherein the surface tension of the solution is between about 10 to 70 dynes/cm, said composition being formulated as a solution in a unit dose for aerosol administration to the nasal sinuses and being packaged with directions for its use in the treatment of sinusitis. The pH of the composition typically ranges from about 3.0 to 8.5. The osmolality typically ranges from 300 mOsm/kg to 880 mOsm/kg, where the NaCl equivalency to the solution is generally between about 0.9% NaCl to 3.0% NaCl. The compositions also contain a surfactant. The compositions can additionally contain other active agents for treatment of sinusitis, such as a decongestant.

In one embodiment, the agent is an anti-infective agent and the sinusitis is caused by a pathogen selected from among *Alpha Hemolytic streptococci, Beta Hemolytic streptococci, Branhamella Catarrhalis, Diptheroids, Haemophilis influenzae* (beta-lactamase positive and negative), *Moraxella* species, *Pseudomonas aeruginosa, Pseudomonas maltophilia, Serratia marcescens, Staphylococcus aureus, Streptococcus pneumonia, Aspergillosis, Mucor* and *Candida Albicans, Fusarium, Curvularia, cryptococcus, coccidioides,* and *histoplasma*. The anti-infective agent can be selected from among Penicillins, Cephalosporins, Macrolides, Sulfonamides, Quinolones, Aminoglycosides, Beta-Lactam antibiotics, Linezolid, Vancomycin, Amphotericin B, and Azole antifungals. The surfactant can be a polysorbate, such as polysorbate 20 to polysorbate 85.

The compositions can be formulated as an aerosol. In one embodiment, at least about 85% of the aerosolized particles have a Mass Median Aerodynamic Diameter within the range of about 1.0 to 4.0 microns. These aerosols can be effective to kill at least about 90% of susceptible sinusitis-causing pathogens present in the sinus passages of a sinusitis patient within about 14 days following an every 8 hr (TID), every 12 hr (BID), or every 24 hr (AD) administration protocol.

Kits containing the compositions are provided. In a one embodiment, a kit is described that provides the various equipment and attachments useful in administering the formulations of the present invention by using the disclosed nebulizer devices. In one embodiment, the kits contain a nebulizer cup with a nasal adapter for delivering the composition in aerosolized form to the nasal sinuses. This kit can be combined with a nebulizer device.

Methods of treatment a patient suspected or diagnosed as having chronic sinusitis are provided. Preferred administration protocols also are described. The pharmaceutical composition, for example, can be administered to the patient 1–3 times a day for a total of 14–21 days. These methods can include the step of administering to the pharmaceutical composition by aerosolization using a nebulizer, which delivers aerosol particles of between about 1 to 5 μm in average diameter. Nebulizers that deliver aerosol particles between about 1 to 5 μm in average diameter are known in the art (see U.S. Pat. No. 5,508,269). One exemplary nebulizer is a PARI nebulizer with a nasal adapter. The nebulizer can be connected to a PARI SinuNEB compressor which is an exemplary device to generate an airflow to deliver the composition. The nebulizer can deliver a majority of aerosolized particles in the size range of abut 3.0 to 3.5 μm in diameter.

DETAILED DESCRIPTION

I. General Description

Figure 1:
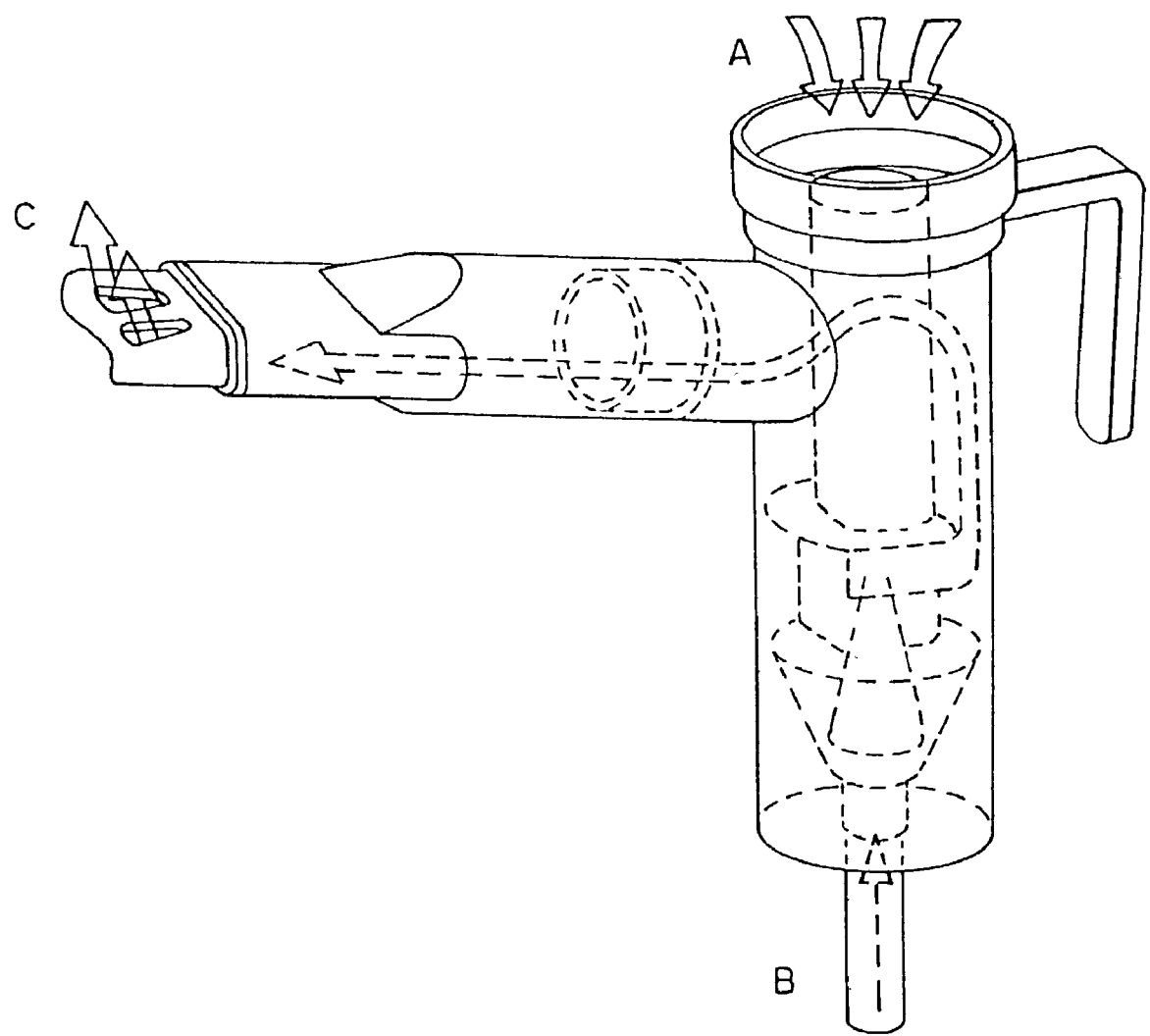
FIG. 1 discloses the preferred equipment for aerosolized delivery of pharmaceutical solutions. This nebulizer, manufactured by Pari Respiratory Equipment, Inc., for the inventors, produces the desired particle size for effective administration of the solutions in this invention to the sinuses. To use this nebulizer preferably medication is placed in the nebulizer at A. The nebulizer is then connected to a compressor or other source at B with tubing supplied. When the airflow is turned on, the patient places the nose piece C under their nostrils and breathes normally until the medication solution in the nebulizer begins to sputter and no mist comes out at C.

The present invention involves the topical delivery of medications to the nasal cavity and sinuses by aerosolizing aqueous solutions of these medications. The present invention is based in part on the surprising finding that aerosolized ant-infective particles are surprisingly effective therapeutically when they have a mass median aerodynamic diameter (MMAD) of about 3.0 to 3.5 μm for deposition in the sinuses in a preferred size range. The present invention provides an apparatus for delivery of such optimally sized anti-infective particles into the sinuses. The present invention is also based in part on the finding that the addition of a surfactant to formulations increases the deposition, retention, and penetration of anti-infectives or other active ingredients into the sinuses. The present invention provides guidance for therapy schedule and dosage as discussed in detail below.

As described in greater detail below, the pharmaceutical formulations will be aerosolized/atomized prior to administration to a patient to form an aerosol cloud with particles of aerosolized/atomized $H_2O$ and medication that have a MMAD (Mass Median Aerodynamic Diameter) of preferably between about 0.5 and 5.0 microns, more preferably between about 1.0 to 4.0 microns and most preferably between about 2.0 to 3.5 microns. It is also preferable to have the maximum number of particles over 5.0 microns be less than 20% of the total particles.

A surprising discovery made by the inventors was that the surface tension of the solution prepared for inhalation needed to be adjusted to achieve optimal results. To achieve effective deposition of medication within the sinuses it is preferable to have the surface tension of the solution for aerosolization be adjusted with surfactants to between 10 dynes/cm and 70 dynes/cm, more preferably between about 20 to 60 dynes/cm, and most preferably between about 30 to 50 dynes/cm.

Contemplated pharmaceutical compositions will include one or more active ingredients such as anti-infective, anti-inflammatory and mucolytic agents. Appropriate medications to be used in the methods according to the present invention are listed in Table 1. These medications may be administered for the treatment of sinusitis, particularly chronic sinusitis, by resolving infection, reducing inflammation or reducing congestion in the nasal cavity and sinuses.

These compositions ideally will be formulated as a solution in a unit dose or multi-dose vial for aerosol administration to the nasal cavity and sinuses and packaged with directions for its use in the treatment of sinusitis. Appropriate compositions for this purpose will be formulated by using surfactants, NaCl or other chemicals entities to adjust the solution for administration to have the following properties:

surface tension preferably between about 10 to 70 dynes/cm, more preferably between about 20 to 60 dynes/cm, and most preferably between about 30 to 50 dynes/cm.

osmolality between about 300 mOsm/kg to 880 mOsm/kg, more preferably between about 400 mOsm/kg to 700 mOsm/kg and most preferably between about 500 mOsm/kg to 600 mOsm/kg.

NaCl equivalency of the solution preferably between about 0.9% NaCl and 3.0% NaCl, more preferably between about 1.1% NaCl and 1.8% NaCl and most preferably between about 1.3% NaCl and 1.7% NaCl.

pH preferably between about 3.0 and 8.5, but may vary according to the properties of the medication used.

A. Surface Tension

The present inventors have found that the surface tension and, to a lesser degree, particle size are critical factors in getting optimal deposition of the formulation in the nasal cavity and sinuses. For example, particles that are too large will deposit in the nasal cavity, but are unlikely to enter the sinuses. Having too low a surface tension increases an aerosolized particle's chance of deposition on the first surface that it comes in contact with, which generally would be tissue or structures in the nasal cavity proximal to the sinuses. In contrast, if the surface tension is too high, much of the aerosolized medication is not deposited within the patient's sinuses and ultimately is deposited in the lungs. If the surface tension is too low most of the aerosolized medication is deposited in the nasal cavity and does not reach the sinuses.

For purposes of preparing formulations according to the present invention, surface tension may be measured by using a Ring Tensiometer or the capillary rise measure method which consists of a capillary tube of known diameter placed into the solution and a measurement of capillary rise taken to provide surface tension. Surface tension will then be adjusted using surfactants to fall within a preferred range in dynes/cm.

B. Osmotic Pressure

Optimal osmotic pressure helps to reduce damage to the epithelia cilia of the sinuses. Although often not present in chronic sinusitis patients, epithelia cilia perform a useful function in the sinuses by moving mucosal fluid out of the sinuses.

For purposes of preparing formulations according to the present invention, osmolality may be measured by using an Osmometer. If necessary, osmolality may then be raised to fall within a preferred range by adding NaCl to the solution.

C. Sodium Chloride Equivalency

Optimal NaCl equivalency (tonicity) works to reduce swelling in the sinuses and nasal cavity by drawing water from the nasal and sinus epithelia, reducing swelling. NaCl equivalency below 0.9% (hypotonic) may cause swelling in the epithelia of the nasal cavity and sinuses. NaCl equivalency above 3.0% would raise the tonicity and osmotic pressure above desirable levels and may cause a burning sensation.

For purposes of preparing formulations according to the present invention, NaCl equivalency will closely follow osmotic pressure and can be measured using the methods described in section B above.

D. pH

In general, the pH would be adjusted if a given medication is either more stable or more effective at a certain pH. *American Hospital Formulary Service* (AFHS) published yearly or the *Hand Book of Injectable Drugs* by Lawrence A. Trissel, © 1994 American Society of Hospital Pharmacists, Inc., which are herein incorporated by reference, provide information regarding the stability or effectiveness of a medication at certain pH.

For the purposes of preparing formulations according to the present invention the pH of the various solutions may need to be adjusted to achieve stability or increase effectiveness. A pH meter, where a probe is placed into the solution and the device gives the pH, will be used to measure pH or pH paper will be used to estimate pH by placing solution on the tape and then comparing to a predeveloped chart of pH colorations. When necessary, pH will then be adjusted to arrive at the most preferable range of pH needed for nasal aerosolization by adding buffering agents.

E. General Preparation of a Unit Dose and Production of Aerosol with Optimal Particle Diameter After determining the medications to be used in the formulation, each ingredient is weighed/measured out individually, added together and dissolved in sterile water for injection. The preparation is then tested to ensure that it is within the parameters established for surface tension, osmolality, pH, and sodium chloride equivalency. This is done by using the appropriate equipment for each test as noted in Sections A to D above. To prepare a unit dose, the ingredients of such formulations generally will be dissolved in a solvent such as water or saline solution, in a volume between about 0.5 and 6.0 mls, more preferably between about 2 and 4 mls and most preferably between about 2.5 and 3.5 mls.

F. Surfactants

The surface tension of a fluid is the tendency of the fluid to "stick" to itself when there is a surface between the liquid and the vapor phase (known as an interface). A good example is a drop of water falling in air. The drop assumes a spherical shape due to surface tension forces, which minimize its surface given the volume. Molecules at the surface of a liquid exert strong attractive forces on other molecules within their vicinity. The resultant force acting perpendicular to a line of unit length in the surface is known as surface tension, usually measured in Dynes/Centimeter.

Surfactants can be used as dispersing agents, solubilizing agents and spreading agents. Some examples of surfactants are: Polyethylene glycol 400; Sodium lauryl sulfate; sorbitan laurate, sorbitan palmitate, sorbitan stearate (available under the tradename SPAN® 20-40-60 etc.); polysorbates including, but not limited to, polyoxyethylene (20) sorbitan monolaurate, polyoxyethylene (20) sorbitan monopalmitate, polyoxyethylene (20) sorbitan monostearate (available under the tradename TWEEN® 20-40-60 etc.); and Benzalkonium chloride. The purpose of using surfactants in the preferred formulations of the present invention is to adjust the surface tension of the aerosolized particles so that the maximum amount of medication is deposited in or near the middle meatus ostea. If the surface tension is reduced too much, the majority of the particles will deposit in the nasal cavity, conversely if the surface tension is too high the particles go directly to the lungs without depositing in the nasal sinuses.

The HLB (hydrophile-lipophile-balance) is used to describe the characteristics of a surfactant. The system consists of an arbitrary scale to which HLB values are experimentally determined and assigned. If the HLB value is low, the number of hydrophilic groups on the surfactant is small, which means it is more lipophilic (oil soluble).

Surfactants can act as solubilizing agents by forming micelles. For example, a surfactant with a high HLB would be used to increase the solubility of an oil in an aqueous medium. The lipophilic portion of the surfactant would entrap the oil in the lipophilic (interior) portion of the micelle. The hydrophilic portion of the surfactant surrounding of oil globule would, in turn, be exposed to the aqueous phase.

An HLB value of 10 or higher means that the agent is primarily hydrophilic, while an HLB value of less than 10 means it would be lipophilic. For example, SPANs have HLB values ranging from 1.8 to 8.6, which is indicative of oil soluble for oil dispersible molecules. Consequently, the oil phase will predominate and a water/oil emulsion will be formed. TWEENs have HLB values that range from 9.6 to 16.7, which is characteristic of water-soluble or water dispersible molecules. Therefore, the water phase will predominate and oil/water emulsions will be formed.

Emulsifying agents are surfactants that reduce the interfacial tension between oil and water, thereby minimizing the surface energy through the formation of globules. Wetting agents, on the other hand, aid in attaining intimate contact between solid particles and liquids.

Detergents are also surfactants that reduce the surface tension and wet the surface as well as the dirt. When a detergent is used, the dirt will be emulsified, foaming may occur and the dirt will then wash away.

G. Pathogens Known to Produce Acute and Chronic Sinus Infections

A retrospective review of sinus cultures obtained over a 4-year period from a consecutive series of patients who underwent endoscopic sinus surgery (ESS) was conducted by Niel Bhattacharyya M.D. et al.; Archives of Otolaryngology-Head and Neck surgery Vol. 125 No. 10, October 1999. A wide range of bacteria may be present in the infected post-ESS sinus cavity, with a considerable population of gram-negative organisms, including *Pseudomonas* species. Fungal infections of the sinuses have a nonspecific clinical presentation, is refractory to standard medical treatment and may produce expansion and erosion of the sinus wall. Various factors have been implicated in the development of fungal sinusitis: anatomical factors in the osteomeatal complex, tissular hypoxia, traumatic factors, massive exposure to fungal spores, allergy and immunosuppression.

The most common bacterial organisms found are the following: *Alpha Hemolytic streptococci, Beta Hemolytic streptococci, Branhamella Catarrhalis, Diptheroids, Haemophilis influenzae* (*beta-lactamase* positive and negative), *Moraxella species, Pseudomonas aeruginosa, Pseudomonas maltophilia, Serratia marcescens, Staphylococcus aureus* and *Streptococcus pneumonia.*

The most common fungal organisms found are the following: *Aspergillosis, Mucor* and *Candida Albicans, Fusarium, Curvularia, cryptococcus, coccidioides*, and *histoplasma.*

The optimum treatment modality is for the physician to obtain a culture from the sinus cavities via endoscope. The culture is sent to a laboratory where it is tested for minimum inhibitory concentration for several antibiotics and then the correct antibiotic can be chosen based on the sensitivities provided by the laboratory. Current therapy by most Otolaryngologists is to determine the best antibiotic by using their clinical experience in treating sinus infections. This is called empiric therapy.

The anti-fungal therapy is done similarly in that it can also be cultured and sent to the lab for identification allowing the most effective agent to be prescribed, or empiric therapy is performed by the physician.

The kill rate is determined by the susceptibility of the organism to the antibiotic or antifungals. If culture and sensitivities are performed and the correct antibiotic is prescribed the kill rate occurs between a period of one to three weeks. The kill is determined/measured by a repeat culture and sensitivity test showing no bacterial or fungal growth (as appropriate).

II. Specific Embodiments

A. Pharmaceutical Compositions and Formulations

Preferred anti-infective agents include Penicillins, Cephalosporins, Macrolides, Sulfonamides, Quinolones, Aminoglycosides, BetaLactam antibiotics, Linezolid, Vancomycin, Amphotericin B, and Azole antifungals. Preferred anti-inflammatory agents include Glucocorticoids, Disodium Cromoglycate and Nedcromil Sodium. Preferred mucolytic agents are Acetylcysteine and Dornase Alpha. Preferred decongestant agents are Phenylephrine, Naphazoline, Oxymetazoline, Tetrahydrozoline and Xylometoazoline. These agents may be found in the *American Hospital Formulary Service* published by American Society of Hospital Pharmacists, Inc., which is incorporated herein by reference.

As an example of a contemplated formulation, Cefuroxime is formulated in dosages of 285 mg in 3 ml sterile water for injection per dose, to produce an antibiotic for aerosol administration. This formulation may be compounded under a Laminar Flow hood by performing the following steps: 1) weigh out sufficient cefuroxime to provide 21 doses of 285 mg each (5985 mg), with 5% overage to account for that lost in compounding; 2) QS ad (add up to) to 63 ml with sterile water, with 5% overfill for loss in compounding; and 3) adding 0.1 ml of polysorbate 20 per 100 ml solution.

The formulation is tested using a Ring Tensiometer or the Capillary Rise test to determine the surface tension of the solution. The preferable range is 10 to 70 dynes/cm. The formulation may be adjusted with a surfactant if necessary using, for example, polysorbate 20. Using a pH meter, the formulation is tested for the desirable pH, preferably in the range of about 3.0 to 8.5. The pH is adjusted with appropriate acids, bases and appropriate buffers as needed according to conventional compounding practices.

Preferably the formulation will also be evaluated using E tables from sources known to practitioners skilled in the pharmaceutical arts, such as Remington: The Science and Practice of Pharmacy or other suitable pharmaceutical text to calculate its sodium chloride equivalence to ensure that it is in the preferred range of 0.9% to 3.0%. Similarly, the osmolality is checked to ensure that it falls within the preferred range of about 300 to 880 mOsm/kg. If osmolality falls outside of this range, the polysorbate 20 component may be decreased until the preferred conditions are met.

As a second example, Ciprofloxacin is formulated in dosages of 90 mg unit dose in 3 ml of sterile water for injection per dose. Because compounds of this antibiotic class (i.e., Fluoroquinolones) do not have inherent surfactant activities, a surfactant preferably is added to lower the surface tension of the final product.

This formulation may be compounded under a Laminar Flow hood by performing the following steps: 1) weighing out a sufficient quantity of Ciprofloxacin powder to prepare 28 doses (2520 mg) with 5% overage to account for loss during compounding; 2) QS ad to 74 ml sterile water for injection (add 5% overage for loss in compounding); and 3) adding 0.25 ml polysorbate 20 for every 100 ml of solution.

The formulation is tested as described above and adjustments made to bring surface tension, pH, sodium chloride equivalence and osmolality within preferred ranges or to preferred levels.

As a third example, Amphotericin B is formulated in 10 mg unit doses along with Hydrocortisone sodium succinate in 50 mg unit doses in 3 ml sterile water to provide an antifungal agent together with an anti-inflammatory agent.

This formulation may be compounded under a Laminar Flow hood by performing the following steps: 1) weighing out sufficient powder of Amphotericin B to make 28 doses (280 mg) of 10 mg each allowing 5% overage for loss in compounding; 2) weighing out sufficient powder of Hydrocortisone sodium succinate to make 28 doses (1400 mg) of 50 mg each allowing 5% overage for loss of compounding; 3) combining powders; and 4) QS ad sterile water for injection to 84 ml plus 5% for loss in compounding. The formulation is tested as described above and adjustments made to bring surface tension, pH, sodium chloride equivalence and osmolality within preferred ranges or to preferred levels.

As a fourth example, Ofloxacin is formulated in 90 mg unit doses along with Acetylcystiene in 100 mg unit doses in 3 ml of sterile water to provide an antibiotic together with a mucolytic agent for injection.

This formulation is compounded under a Laminar Flow Hood by performing the following steps: 1) weighing out sufficient powder of Ofloxacin to make 28 doses (2520 mg) of 90 mg each allowing 5% overage for loss in compounding; 2) weighing out sufficient powder of Acetylcysteine to make 28 doses (2800 mg) of 100 mg each allowing 5% overage for loss in compounding; and 3) combining the powders and QS ad to 84 ml with sterile water for injection allowing 5% overage for loss during compounding. The formulation is tested as described above and adjustments made to bring surface tension, pH, sodium chloride equivalence and osmolality within preferred ranges or to preferred levels.

As a fifth example, Tobramycin is formulated in 100 mg unit doses in 2.5 ml of saline solution to provide an alternative antibiotic formulation. The formulation is compounded under a Laminar Flow hood by performing the following steps: 1) weighing out the tobramycin powder sufficient to provide 42 doses of 100 mg per dose (4200 mg), allowing for 5% overage due to losses during compounding; 2) QS ad with 105 ml of sterile water for injection, allowing for 5% overage due to losses during compounding; and 3) adding 0.15 ml polysorbate 20 to adjust surface tension. The formulation is tested as described above and adjustments made to bring surface tension, pH, sodium chloride equivalence and osmolality within preferred ranges or to preferred levels.

As a sixth example, Cefoperazone and Oxymetazoline are formulated in 3 ml of Sterile water for injection to provide an antibiotic formulated with a decongestant. This formulation is prepared under a Laminar Flow Hood by following these steps: 1) weighing out sufficient powder of Cefoperazone to make 28 doses of 600 mg each (16.8 gm) allowing 5% overage for compounding loss; 2) weighing out sufficient powder of Oxymetazoline to make 28 doses of 0.5 mg each (14 mg) allowing 5% overage for compounding loss; 3) combining the powders together; 4) QS ad with sterile water to 84 ml allowing 5% overage for compounding loss; 5) adding Benzalkonium Chloride 0.02% (0.02 gm/100 ml of solution). The formulation is tested as described above and adjustments made to bring surface tension, pH, sodium chloride equivalence and osmolality within preferred ranges or to preferred levels.

B. Determination of the Course of Treatment

In general, the course of treatment for any given patient will be determined by his or her physician. Thus, if the organisms found in a patient's sinuses are cultured by known techniques and their sensitivities are determined, the most appropriate antibiotic will be ordered. However, if no cultures and sensitivities are done, then the patient also may be treated empirically with the antibiotic chosen by the physician using his or her experience based on what bacteria or fungus is suspected. If the anatomical structures inside the nasal passageways are swollen or inflamed due to allergy or flu symptoms, an anti-inflammatory agent or a decongestant agent also may be administered if the patient is not otherwise using nasal sprays or oral medication separately.

Example of a Patient Treatment Scenario

1. Patient contracts what they feel is a sinus infection and goes to their Otolaryngologist for diagnosis. After determining the diagnosis of sinusitis, a culture is obtained endoscopically and sent to the laboratory.

2. The laboratory determines the bacteria/fungus sensitivities by drug and reports its findings to the physician.

3. The physician faxes the report to the pharmacy along with a prescription for the antibiotic most appropriate for the infection. The formulation is prepared as described above and dispensed in 2.5 ml containers. Generally, the container will be labeled: "Store in Refrigerator."

4. The physician will call patient and discuss the treatment and any pertinent data necessary to enhance the treatment outcome.

C. Contemplated and Preferred Treatment Regimens

The preferred treatment is the antibiotic (adjusted for the proper surface tension, pH, sodium chloride equivalence, and osmolality) that most effectively kills the bacteria or fungus as determined by culture and sensitivity, administered once to three times per day for a duration of 5 to 10 minutes per each treatment (See Table 1).

The total number of days needed to rid the infection preferably is determined by reculturing until no growth is noted. However, when the physician does not do culturing, the conventional standard of practice is two weeks of therapy until patient generally would be expected to have become asymptomatic plus an additional 7 days of therapy.

D. Monitoring Efficacy

The typical Otolaryngologist when treating chronic sinusitis prescribes antibiotics until the patient is symptom free by physical exam plus an additional seven days. The problem that occurs with respect to sinus infections is that, if the infection is not completely resolved, the patient will have a recurrence the next time their immune system is challenged, i.e., they contract the flu, go through a stressful time in their life or need chemotherapy treatments. Thus, the preferred method of determining resolution of the infection is to reculture the sinuses endoscopically and have the laboratory report come back negative, i.e., reporting no growth of pathogenic microorganisms. The present inventors have discovered that aerosolization should lead to less resistance exhibited by bacteria due to the fewer times they are exposed to the antibiotic, and such exposure occurs at lower dosages and for shorter periods of time of aerosolized administration (typically 1–3 weeks) as compared to oral (typically 3 weeks to several months) and intravenous treatment (typically 3–6 weeks).

E. Equipment for Aerosolized Delivery of Pharmaceutical Composition

Equipment for aerosolized delivery of pharmaceutical compositions are well known to the skilled artisan. O'Riordan et al., *Journal of Aerosol Medicine*, 20(I):13–23 (1997), reports the delivery of aerosolized tobramycin by a jet nebulizer and an ultrasonic nebulizer. U.S. Pat. No. 5,508,269, issued Apr. 16, 1996, compares the characteristics of three different nebulizers: the Ultraneb 99 (DeVilbiss)

ultrasonic nebulizer, the Medicaid Sidestream jet nebulizer, and the Pari LC jet nebulizer.

The preferred equipment for aerosolized delivery of pharmaceutical solutions is depicted in FIG. 1. This nebulizer manufactured by Pari Respiratory Equipment, Inc for the inventors produces the desired particle size for effective administration of the solutions in this invention to the sinuses. To use this nebulizer preferably 1 ml to 5 ml of medication solution, more preferably 2 ml to 4 ml and most preferably 2.5 ml to 3.5 ml of medication solution is placed in the nebulizer at A. The nebulizer is then connected to a compressor or other source of 4 liter/minute airflow at B with tubing supplied. When the airflow is turned on the patient places the nose piece C under their nostrils and breathes normally until the medication solution in the nebulizer begins to sputter and no mist comes out at C. This will usually take 8 to 10 minutes.

In light of the foregoing general discussion, the specific examples presented below are illustrative only and are not intended to limit the scope of the invention. Other generic and specific configurations will be apparent to those persons skilled in the art.

EXAMPLES

Example 1

Patient A

A female in her forties had been suffering from sinusitis for most of her adult life. These sinusitis episodes seemed to be triggered by allergies. She historically had three-four (3–4) episodes of sinusitis each year, which were treated with oral antibiotics for four-eight (4–8) weeks per episode. These oral antibiotic regimens produced yeast infections, which were treated with Diflucan® (fluconazole). Relief from the headaches, malaise, facial pressure and pain, yellow-green nasal discharge, coughing and fever took up to six weeks and were treated with narcotic and non narcotic analgesics, decongestants, decongestant nasal sprays, cough suppressants, and nasal rinses. Her allergies were treated with antihistamines and anti-inflammatory agents.

In an effort to reduce the duration of her sinusitis episodes, a nose drop of tobramycin 80 mg/ml was administered. This treatment did not seem to work. The medication was irritating; and in order to administer the drops and try to get them into the sinus cavity, the patient had to hold her head back. This caused intolerable pain resulting in the discontinuation of the therapy. A nose drop of Bactoban® (Mupirocin calcium 2%) was tried. It was not efficacious; it was very viscous. The administration of this drop produced similar pain on administration, and this therapy was also discontinued.

In order to eliminate the pain caused by holding her head back when administering nose drops, a nose drop of tobramycin was administered after the patient had been on oral antibiotics for a period of time. This did not seem to work. The drop did not seem to penetrate into the sinus cavities.

Thereafter, a preparation of tobramycin 80 mg/ml was administered using 3 ml in a Pari LC Star® nebulizer cup with adult mask attached and a Pari Proneb® compressor. The medication was nebulized three (3) times daily. After four days of therapy, the patient experienced a "dumping" of green, purulent nasal discharge. The therapy was continued for a total of seven (7) days. It seemed at this point that the sinus infection had been eliminated, but a relapse was experienced within a month. Another seven (7) day regimen of nebulized tobramycin was given to the patient. Again the sinus infection seemed to be eliminated, but it reoccurred within two (2) months.

A preparation of cefuroxime 285 mg in 2.5 ml sterile water for injection was administered three (3) times daily using a Pari LC Star® nebulizer cup with adult mask attached and a Pari Proneb® compressor. The time of nebulization was extensive and the medication did not seem to be completely nebulized. After one day of therapy, a Pari Turbo® compressor was substituted for the Pari Proneb® compressor. The patient experienced a "dumping" of green, purulent nasal discharge after (3) days of therapy. The therapy was continued for a total of seven (7) days, again she contracted a yeast infection and was given Diflucan®.

After the seven (7) days of treatment with nebulized cefuroxime using the Pari Turbo® compressor and the Pari LC Star® nebulizer cup with mask, the patient has remained free of sinus infections for nine (9) months. She has continued to experience problems with her allergies, and while in the past these allergies triggered sinus infections, this time no such infection has recurred.

Example 2

Patient B

A male in his forties had been experiencing sinus infections off and on during his adult life. He was treated with cefuroxime 285 mg in 2.5 ml of sterile water for injection three (3) times daily using a Pari LC Star® nebulizer cup with adult mask attached and a Pari Turbo® compressor. The patient experienced a "dumping" of green, purulent nasal discharge after eight (8) treatments. The therapy was continued for a total of seven (7) days. No other antibiotics were given. This patient has been free from sinus infections for six (6) months.

Example 3

Patient C

A female aged mid-50s had been suffering from sinusitis off and on for most of her adult life. These sinusitis episodes seemed to be triggered by allergies. The patient took antihistamines and decongestants when allergies triggered headaches and/or a clear nasal discharge. Historically, she would have one or more sinus infections a year requiring twenty or more days of oral antibiotics.

She was treated with cefuroxime 285 mg in 2.5 ml of sterile water for injection three (3) times daily using a Pari LC Star® nebulizer cup with adult mask attached and a Pari Turbo® compressor. The patient experienced a "dumping" of green, purulent nasal discharge after eight (8) treatments. The therapy was continued form a total of seven (7) days. No other antibiotics were given. This patient has been free from sinus infections for six (6) months.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents and patent applications that are identified in this patent application are incorporated by reference in their entirety.

TABLE 1

Agents and Dosages

| Generic Name | Brand Name | Class | Preferable Range | More Preferable Range | Most Preferable Range | Most Preferable Dose |
|---|---|---|---|---|---|---|
| Amikacin | Amikin | Aminoglycoside | 50–500 mg | 75–300 mg | 100–200 mg | 166 mg Q8–12H |
| Amphotericin B | Fungizone | Antifungal | 2.5–45 mg | 4–30 mg | 7.5–15 mg | 10 mg Q12H |
| Azithromycin | Zithromax | Macrolide | 50–400 mg | 75–300 mg | 150–200 mg | 167 mg Q12H |
| Aztreonam | Azactam | Monobactam | 250–1000 mg | 300–900 mg | 475–750 mg | 450 mg Q8H |
| Cefazolin | Ancef, Kefzol | Cephlasporin (Gen I) | 250–1000 mg | 300–900 mg | 575–700 mg | 650 mg 08H |
| Cefepime | Maxipime | Cephlasporin (Gen IV) | 125–1000 mg | 200–900 mg | 575–700 mg | 650 mg Q12H |
| Cefonicid | Moniacid | Cephlasporin (Gen II) | 250–1000 mg | 300–900 mg | 575–700 mg | 600 mg Q24H |
| Cefoperazone | Cefobid | Cephlasporin (Gen III) | 250–1000 mg | 300–900 mg | 575–700 mg | 600 mg Q12H |
| Cefotaxime | Claforan | Cephlasporin (Gen III) | 250–1000 mg | 300–900 mg | 575–700 mg | 600 mg Q8–12H |
| Cefotetan | Cefotan | Cephlasporin (Cephamycin) | 250–1000 mg | 300–900 mg | 575–700 mg | 600 mg Q8–12H |
| Cefoxitin | Mefoxin | Cephlasporin (Cephamycin) | 250–1000 mg | 300–900 mg | 575–700 mg | 600 mg Q12H |
| Ceftazidime | Fortaz, Ceptaz | Cephlasporin (Gen III) | 250–1000 mg | 300–900 mg | 475–750 mg | 550 mg Q12H |
| Ceftizoxime | Cefizox | Cephlasporin (Gen III) | 250–1000 mg | 300–900 mg | 575–700 mg | 600 mg Q8–12H |
| Ceftriaxone | Rocephin | Cephlasporin (Gen III) | 250–1000 mg | 300–900 mg | 575–700 mg | 650 mg Q12H |
| Cefuroxime | Ceftin | Cephlasporin (Gen II) | 100–600 mg | 200–520 mg | 250–400 mg | 285 mg Q8H |
| Cephapirin | Cefadyl | Cephlasporin (Gen I) | 250–1000 mg | 300–900 mg | 575–700 mg | 650 mg Q12H |
| Ciprofloxacin | Cipro | Quinolone | 25–200 mg | 50–175 mg | 75–110 mg | 90 mg Q12H |
| Clindamycin | Cleocin | Lincosamide | 50–600 mg | 75–500 mg | 125–300 mg | 225 mg Q12H |
| Doxycycline | Vibramycin | Tetracycline | 10–100 mg | 15–80 mg | 25–65 mg | 27 mg Q12H |
| Fluconazole | Diflucan | Antifungal | 12.5–150 mg | 20–70 mg | 25–50 mg | 30 mg Q12H |
| Gentamycin | Garamycin | Aminoglycoside | 10–200 mg | 30–150 mg | 80–120 mg | 95 mg Q8–12H |
| Itraconazole | Sporanox | Antifungal | 12.5–150 mg | 20–70 mg | 25–50 mg | 30 mg Q12H |
| Levofloxacin | Levaquin | Quinolone | 40–200 mg | 50–150 mg | 60–80 mg | 70 mg Q12H |
| Meropenem | Merrin | Carbapenem | 200–750 mg | 250–700 mg | 300–500 mg | 333 mg Q8H |
| Mezlocillin | Mezlin | Penicillin | 300–1500 mg | 375–1000 mg | 750–950 mg | 833 mg Q6H |
| Miconazole | Monistat | Antifungal | 12.5–300 mg | 30–200 mg | 50–100 mg | 60 mg Q12H |
| Nafcilin | Nafcil | Penicillin | 100–1000 mg | 125–750 mg | 250–600 mg | 460 mg Q6H |
| Ofloxacin | Floxin | Quinolone | 25–200 mg | 50–175 mg | 75–110 mg | 90 mg Q12H |
| Piperacillin | Pipracil | Penicillin | 100–1000 mg | 125–750 mg | 250–600 mg | 460 mg Q6H |
| Rifampin | Rafadin | Miscellaneous | 500–5000 mg | 1000–4000 mg | 1500–3500 mg | 2250 mg Q12H |
| Ticarcillin + Clavulanate | Timentin | Penicillin | 500–5000 mg | 1000–4000 mg | 1500–3500 mg | 2250 mg Q6–8H |
| Tobramycin | Nebcin | Aminoglycoside | 10–200 mg | 30–150 mg | 80–120 mg | 95 mg Q8–12H |
| Vancomycin | Vancocin | Antifungal | 50–400 mg | 75–325 mg | 125–250 mg | 166 mg Q6–8H |

What is claimed is:

1. An aerosolized pharmaceutical solution, comprising: aerosolized particles of the solution, which contains an antibiotic for treating sinusitis, and a surfactant, wherein:

the solution is formulated for nasal administration as an aqueous solution;

the solution as formulated has an osmolality of about 300 mOsm/kg to about 880 mOsm/kg;

the solution as formulated has a surface tension of about 30 to about 50 dynes/cm, wherein the surface tension is effective for retention of the solution in the nasal sinuses;

the solution as formulated contains at least about 0.02% (w/v) surfactant;

the antibiotic for treating sinusitis is selected from the group consisting of aminoglycosides;

and wherein at least about 80% of the aerosolized particles of the pharmaceutical solution have a mass median aerodynamic diameter (MMAD) in the size range of about 0.5 µm to about 5.0 µm in diameter, whereby the aerosolized pharmaceutical solution is effective for treatment of chronic sinusitis.

2. The solution of claim 1, wherein the solution further comprises an anti-infective, an anti-inflammatory, a mucolytic agent or a combination thereof.

3. The solution of claim 1, wherein the solution is formulated for administration via a nebulizer.

4. The solution of claim 1, wherein the solution has a pH of about 3.0 to about 8.5.

5. The solution of claim 1, wherein the solution further comprises a decongestant.

6. The solution of claim 1, wherein at least about 80% of the particles have a mass median aerodynamic diameter (MMAD) in the size range of about 1.0 µm to about 4.0 µm in diameter.

7. The solution of claim 1, wherein at least about 80% of the particles have a mass median aerodynamic diameter (MMAD) in the size range of about 2.0 µm to about 3.5 µm in diameter.

8. The solution of claim 1, wherein less than about 20% of the total particles have a mass median aerodynamic diameter (MMAD) of greater than 5 µm.

9. The solution of claim 1, wherein the solution has an osmolality of about 150 mOsm/kg to about 880 mOsm/kg.

10. The solution of claim 1, wherein the solution has an osmolality of about 400 mOsm/kg to about 700 mOsm/kg.

11. The solution of claim 1, wherein the solution has an osmolality of about 500 mOsm/kg to about 600 mOsm/kg.

12. The solution of claim 1, wherein the solution has an NaCl equivalency of about 1.1% NaCl to about 1.8% NaCl.

13. The solution of claim 1, wherein the solution has an NaCl equivalency of about 1.3% NaCl to about 1.7% NaCl.

14. The solution of claim 1, wherein the Aminoglycoside is selected from the group consisting of Amikacin, Gentamycin and Tobramycin.

15. The solution of claim 1, wherein the surfactant comprises polysorbate.

16. The solution of claim 2, wherein the anti-inflammatory agent comprises a glucocorticoid, disodium cromoglycate, nederomil sodium or a combination thereof.

17. The solution of claim 2, wherein the mucolytic agent comprises acetylcysteine, dornase alpha, or a combination thereof.

18. The solution of claim 5, wherein the decongestant comprises phenylephrine, naphazoline, oxymetazoline, tetrahydrozoline, xylometoazoline, or a combination thereof.

19. The solution of claim 1, wherein the surfactant comprises polyethylene glycol 400, sodium lauryl sulfate, sorbitan esters, polysorbates, benzalkonium or a combination thereof.

20. The solution of claim 1, wherein the surfactant has a hydrophile-lipophile-balance (HLB) of between about 1.8 to about 8.6.

21. The solution of claim 1, wherein the surfactant has a hydrophile-lipophile-balance (HLB) of between about 9.6 to about 16.7.

22. The solution of claim 2, wherein the anti-infective is selected from the group consisting of Penicillins, Cephalosporins, Macrolides, Sulfonamides, Quinolones, aminoglycosides, BetaLactam antibiotics, Linezolid, Vancomycin, Amphotericin B, and Azole antifungals or a combination thereof.

23. The solution of claim 1, wherein the solution has an NaCl equivalency of about 0.9% to about 3.0% NaCl.

24. A pharmaceutical solution, comprising: a mucolytic agent for treating sinusitis, and a surfactant, wherein:

the pharmaceutical solution is formulated as an aqueous solution for nasal administration;

the mucolytic agent comprises acetylcysteine, dornase alpha and combinations thereof:

the pharmaceutical solution as formulated has a surface tension from about 30 to about 50 dynes/cm, whereby the surface tension is effective for retention of the agent in the nasal sinuses; and the pharmaceutical solution, upon aerosol administration, is effective for treatment of chronic sinusitis;

the solution as formulated contains at least about 0.02% (w/v) surfactant;

and 80% of the aerosolized particles of the pharmaceutical solution have a mass median aerodynamic diameter (MMAD) in the size range of about 0.5 µm to about 5.0 µm in diameter.

25. The solution of claim 24, wherein the solution is formulated as a solution in a unit dosage for aerosol administration to nasal sinuses.

26. The solution of claim 24, wherein the solution is formulated for administration via a nebulizer.

27. A solution of claim 24, wherein at least about 80% of the particles that have a mass median aerodynamic diameter (MMAD) in the size range of about 1.0 µm to about 4.0 µm in diameter.

28. An aerosolized solution of claim 24, wherein at least about 80% of the particles have a mass median aerodynamic diameter (MMAD) in the size range of about 2.0 µm to about 3.5 µm in diameter.

29. The solution of claim 24, wherein less than about 20% of the total particles in the aerosol have a mass median aerodynamic diameter (MMAD) of greater than 5 µm.

30. The solution of claim 24, wherein the solution has a pH of about 3.0 to about 8.5.

31. The solution of claim 24, wherein the solution has an osmolality of about 150 mOsm/kg to about 880 mOsm/kg.

32. The solution of claim 24, wherein the solution has an osmolality of about 300 mOsm/kg to about 880 mOsm/kg.

33. The solution of claim 24, wherein the solution has an osmolality of about 400 mOsm/kg to about 700 mOsm/kg.

34. The solution of claim 24, wherein the solution has an osmolality of about 500 mOsm/kg to about 600 mOsm/kg.

35. The solution of claim 24, wherein the solution has an NaCl equivalency of about 0.9% NaCl to about 3.0% NaCl.

36. The solution of claim 24, wherein the surfactant comprises polyethylene glycol 400, sodium lauryl sulfate, sorbitan esters, polysorbates, benzalkonium or a combination thereof.

37. The solution of claim 24, wherein the surfactant comprises polysorbate.

38. The solution of claim 24, wherein the surfactant has a hydrophile-lipophile-balance of between about 1.8 to about 8.6.

39. The solution of claim 24, wherein the surfactant has a hydrophile-lipophile-balance of between about 9.6 to about 16.7.

40. The solution of claim 24, wherein the solution further comprises a decongestant.

41. The solution of claim 40, wherein the decongestant comprises phenylephrine, naphazoline, oxymetazoline, tetrahydrozoline, xylometoazoline, or a combination thereof.

42. The solution of claim 24, wherein the solution further comprises an anti-infective, an anti-inflammatory or a combination thereof.

43. The solution of claim 42, wherein the anti-infective is selected from the group consisting of Penicillins, Cephalosporins, Macrolides, Sulfonamides, Quinolones, aminoglycosides, BetaLactam antibiotics, Linezolid, Vancomycin, Amphotericin B, Azole antifungals and a combination thereof.

44. The solution of claim 42, wherein the anti-inflammatory agent comprises a glucocorticoid, disodium cromoglycate, nedcromil sodium or a combination thereof.

45. The solution of claim 1, wherein the antibiotic is tobramycin.

46. The solution of claim 1, wherein the solution is formulated for single dosage administration.

47. The solution of claim 46, wherein the antibiotic is tobramycin.

* * * * *